United States Patent
McManus et al.

(10) Patent No.: US 7,141,769 B2
(45) Date of Patent: Nov. 28, 2006

(54) SPECTROSCOPY-BASED REAL-TIME CONTROL FOR MICROWAVE-ASSISTED CHEMISTRY

(75) Inventors: Michael E. McManus, Waxhaw, NC (US); Michael J. Collins, Sr., Matthews, NC (US); Michael J. Collins, Jr., Charlotte, NC (US)

(73) Assignee: CEM Corporation, Charlotte, NC (US)

( * ) Notice: Subject to any disclaimer, the term of this patent is extended or adjusted under 35 U.S.C. 154(b) by 0 days.

(21) Appl. No.: 11/097,859

(22) Filed: Apr. 1, 2005

(65) Prior Publication Data

US 2006/0219710 A1 Oct. 5, 2006

(51) Int. Cl.
  *H05B 6/80* (2006.01)
(52) U.S. Cl. ................................. 219/704; 219/687
(58) Field of Classification Search ............... 219/704, 219/687, 696, 711, 726, 745, 746, 679, 718; 34/393; 422/129, 186, 187, 186.29; 356/301, 356/419; 436/148, 164; 210/295
  See application file for complete search history.

(56) References Cited

U.S. PATENT DOCUMENTS

| | | | |
|---|---|---|---|
| 3,020,645 A | 2/1962 | Copson | |
| 4,507,531 A * | 3/1985 | Teich et al. ................. | 219/718 |
| 5,972,711 A | 10/1999 | Barclay et al. | |
| 6,227,041 B1 | 5/2001 | Collins et al. | |
| 6,288,379 B1 | 9/2001 | Greene et al. | |
| 6,529,276 B1 * | 3/2003 | Myrick ....................... | 356/419 |
| 6,630,652 B1 | 10/2003 | Jennings | |
| 6,649,889 B1 | 11/2003 | Jennings | |
| 6,713,739 B1 | 3/2004 | Jennings | |
| 6,753,517 B1 | 6/2004 | Jennings | |
| 6,858,436 B1 * | 2/2005 | Zenhausern et al. ........ | 436/164 |
| 6,867,400 B1 | 3/2005 | Collins et al. | |
| 2001/0020599 A1 * | 9/2001 | Lautenschlager ........... | 210/295 |
| 2003/0116027 A1 | 6/2003 | Brulls | |
| 2003/0170149 A1 | 9/2003 | Jennings | |
| 2003/0199099 A1 * | 10/2003 | King et al. .................. | 436/148 |
| 2004/0020923 A1 * | 2/2004 | Collins et al. .............. | 219/687 |
| 2005/0045625 A1 | 3/2005 | Collins et al. | |
| 2005/0176938 A1 * | 8/2005 | Kamada et al. ............. | 536/7.1 |
| 2005/0248758 A1 * | 11/2005 | Carron et al. ............... | 356/301 |

OTHER PUBLICATIONS

Handbook of Vibrational Spectroscopy; John Chalmers and Peter Griffiths; eds., 2001.
Handbook of Raman Spectroscopy: From the Research Laboratory to the Process Line; Ian R. Lewis and Howell G.M. Edwards, eds., 2001.
Christopher M. Stellman et al., In Situ Spectroscopic Study of Microwave Polymerization; Applied Spectroscopy, 1995, vol. 49, No. 3.

(Continued)

*Primary Examiner*—Quang Van
(74) *Attorney, Agent, or Firm*—Summa, Allan, & Addition, P.A.

(57) ABSTRACT

The invention is an instrument and method for microwave-assisted chemical synthesis. The instrument includes a source of microwave radiation for applying microwave energy to a sample, a microwave cavity in wave communication with the source for holding the sample during the application of microwave energy, and a substantially monochromatic radiation source in electromagnetic communication with the cavity for applying substantially monochromatic light to the sample. The instrument further includes a detector positioned to detect Raman scattering of light from the monochromatic source by the sample, and a controller in signal communication with the microwave energy source and the Raman scattering detector for moderating the application of microwave energy to the sample based upon the detected Raman scattering.

52 Claims, 6 Drawing Sheets

OTHER PUBLICATIONS

Don E. Pivonka et al.; Real-Time in Situ Raman Analysis of Microwave-Assisted Organic Reactions; Applied Spectroscopy, 2004, vol. 58, No. 1.

Dorf, The Electrical Engineering Handbook, Second Ed., (1997), CRC Press LLC, USA.

Wolf, Silicon Processing for the VLSI Era, (1990), Lattice Press.

Advantage NIR Raman Spectometer; www.deltanu.com/advantageNIR.htm.

Euclidean geometry—Wikipedia, the free encyclopedia; http://en.wikipedia.org/wiki/Euclidean_geometry.

Posamentier, Advanced Euclidean Geometry: Excursions for Secondary Teachers and Students, 2005, Key Curriculum Press.

Avalon Instruments Website; www.avaloninst.com, 5 pages.

JASCO Website, Raman Spectroscopy Primer, www.jascoraman.com, 10 pages.

* cited by examiner

SPECTROSCOPY-BASED REAL-TIME CONTROL FOR MICROWAVE-ASSISTED CHEMISTRY

BACKGROUND OF THE INVENTION

The present invention relates to microwave-assisted chemistry, and in particular relates to the measurement and control of ongoing microwave-assisted chemical reactions.

As generally recognized in the chemical arts, many chemical reactions can be initiated or accelerated by increasing the temperature (i.e., heating) of the reactants. Accordingly, carrying out chemical reactions at elevated (i.e., above ambient) temperatures is a normal part of many chemical processes.

The benefit of using microwave energy for elevating the temperature of a chemical reaction is well known. For example, U.S. Pat. No. 6,753,517 to Jennings, incorporated entirely herein by reference, discloses a microwave-assisted chemical synthesis instrument using controlled microwave energy.

Additionally, recent developments have increased the use of microwave energy for initiating, accelerating, or maintaining chemical reactions apart from temperature elevation. In some cases, microwaves are usefully applied while keeping reaction temperatures moderate, or even cool (i.e., at or below room temperature).

Monitoring various parameters of microwave-assisted chemistry can be helpful in controlling the input of microwave energy. For example, U.S. Pat. No. 5,972,711 to Barclay et al., also incorporated entirely herein by reference, describes a method for microwave-assisted chemical processes that includes monitoring the temperature of a mixture of reagents to maintain the reagents at or closely about a predetermined temperature.

In another example, U.S. Pat. No. 6,227,041 to Collins et al., also incorporated entirely herein by reference, describes a method and apparatus for measuring volatile content of samples. The method includes monitoring the weight and temperature of the sample during the application of microwave energy. The method further includes moderating the application of microwave power based on the measured temperature to prevent burning the sample.

In yet another example, U.S. Pat. No. 6,288,379 to Greene et al., also incorporated entirely herein by reference, describes a method for the use of continuously variable power in microwave-assisted chemistry. The method includes measuring and moderating the duty cycle of applied microwave power based on a measured selected parameter of a sample at a predetermined set point. The preferred measured parameters include temperature and pressure.

The aforementioned instruments and methods are exemplary for their respective applications. In addition, all benefit from a feedback control mechanism. The feedback control mechanism is based on at least one measured parameter, which may include temperature, pressure, volatile content, or weight, by means of example. These parameters are measured using standard instruments, e.g., an infrared pyrometer for measuring temperature and a pressure transducer for measuring pressure.

Chemical processes are commonly evaluated with respect to contaminants and product yield, for example. In this regard, spectrometers are well known to evaluate and monitor chemical samples, processes, or both for these and other criteria. Defined in general terms, spectroscopy is the physics of the theory and interpretation of interactions between matter and electromagnetic radiation. Electromagnetic radiation may be considered a stream of energy called quanta or photons. The amount of energy in each quantum determines the wavelength of the radiation.

Electrons orbiting atoms typically occupy a "ground state," or the lowest energy level. Bonding between atoms forms a molecule, resulting in a new electron ground state energy level. Under certain conditions, an electron may acquire energy which elevates it to a higher energy level (i.e., an "excited state"). Electrons in atoms, functional groups, or molecules may change their energy level only when distinct quanta of radiation are absorbed or emitted by the molecule. The frequency of the absorbed or emitted radiation is a direct function of the change in energy of the electron. Thus, spectroscopy is the measurement of absorption and emission spectra. Because the amounts of energy absorbed or emitted are characteristic of particular atoms, molecules, and functional groups, spectroscopy is widely used to identify and quantify chemical compositions.

Based on wavelength, technique, or both, many different kinds of spectroscopy are scientifically useful. These include, but are not limited to, infrared (IR) absorption spectroscopy, fluorescence spectroscopy, ultraviolet/visible (UV/VIS), and Raman spectroscopy.

U.S. Patent Publication No. 2003/0116027 to Brulls discloses a method of monitoring a freeze drying process utilizing spectroscopy. The Brulls patent publication discloses that real-time spectroscopic analysis of the freeze-drying process may be used for feedback control of the process based on extracted measurement values, such as temperature and moisture content.

Microwave-assisted chemical synthesis is commonly performed in sealed reaction vessels. This presents a problem with respect to measuring certain reaction parameters, e.g., contaminant formation via side reactions and product yield. Currently, microwave-assisted techniques must monitor these and other parameters using an invasive technique or at least some physical contact with the vessel or its contents (e.g., a pressure transducer). See U.S. Pat. No. 6,630,652 to Jennings, for example.

Spectroscopy is a useful method to non-invasively monitor a reaction in progress. The reaction vessel is typically made of a microwave-transparent material, such as glass or quartz. Some spectroscopy methods, however, such as UV/VIS and IR spectroscopy, are impeded by glass because glass forms an opaque barrier to these wavelengths. Therefore, where glass vessels are desired or necessary, UV and IR spectroscopy are less attractive and potentially useless. Raman spectroscopy is an attractive alternative to U/VIS and IR in this respect because glass is substantially transparent to many of the frequencies commonly used for Raman spectroscopy.

Briefly, Raman spectroscopy measures the vibrational energies of molecules differently than other spectroscopic methods. Raman spectroscopy is based on the measurement of inelastic, as opposed to elastic, scattering of photons by molecules. Scattering occurs following a collision between incident photon energy from an energy source, such as a laser, and a molecule. Elastic scattering of photons occurs when the incident photon energy equals the energy of the photons scattered in all directions after the collision. In this case, the scattered photons provide no information about the molecule.

In contrast, inelastic scattering occurs when incident photons gain or lose energy upon collision with a molecule. In this case, the scattered photons do provide information about the molecule. An in-depth review of the theory and practice of Raman spectroscopy is set forth in *Handbook of*

*Vibrational Spectroscopy* (John Chalmers and Peter Griffiths, eds., 2001) and *Handbook of Raman Spectroscopy: From the Research Laboratory to the Process Line* (Ian R. Lewis and Howell G. M. Edwards, eds., 2001).

Raman spectroscopy has been utilized in microwave-assisted techniques to a limited extent. Stellman et al., used Raman spectroscopy to monitor microwave curing of an amine-cured epoxide as a function of time (Christopher M. Stellman et al., *In Situ Spectroscopic Study of Microwave Polymerization*, Applied Spectroscopy, (49)3, 1995). In this study, Raman spectra of the microwave-cured epoxy were continuously taken in situ over a 2.4 minute curing time. Spectra taken after this time frame (i.e., longer exposure) were discarded because the sample ignited from excess heat accumulation.

More recently, Pivonka and Empfield integrated a Raman probe with a commercial microwave synthesizer to provide real-time spectral feedback from organic reactions for real-time in situ analysis of yield, mechanisms, and kinetics in the microwave-assisted reactions (Don E. Pivonka and James R. Empfield, *Real-Time in situ Raman Analysis of Microwave-assisted Organic Reactions*, Applied Spectroscopy, (58)1, 2004).

The problem that persists in light of these references is the lack of a commercially viable instrument and method for non-invasive real-time feedback control of microwave-assisted chemical synthesis. Logically, another problem that follows is the lack of an instrument and method for self-optimizing microwave-assisted chemical synthesis based on real-time non-invasive spectral analysis.

SUMMARY AND OBJECTS OF THE INVENTION

The invention is an apparatus for microwave-assisted chemical synthesis, including a source of microwave radiation for applying microwave energy to a sample, a microwave cavity in wave communication with the source for holding the sample during the application of microwave energy, a substantially monochromatic radiation source in electromagnetic communication with said cavity for applying substantially monochromatic light to the sample, a detector positioned for detecting Raman scattering of light from said monochromatic source by the sample, and a controller in signal communication with said microwave energy source and said Raman scattering detector for moderating the application of microwave energy to the sample based upon the detected Raman scattering.

The invention is further a method for microwave-assisted chemical synthesis. The method includes applying microwave energy to sample reactants, propagating substantially monochromatic radiation to the sample reactants, measuring the Raman scattering of the monochromatic light from the sample, and moderating the application of microwave energy to the sample based upon the measured Raman scattering.

Therefore, it is an object of the present invention to provide a microwave-assisted chemical synthesis instrument that irradiates a sample with electromagnetic radiation (e.g., radiation from a laser source) and a detector for detecting at least some of the radiation from the sample.

It is a further object of the present invention to provide a microwave-assisted chemical synthesis instrument that receives and analyzes data from the radiation detector and controls the application of microwave energy based on the received data.

It is a further object of the present invention to provide a microwave-assisted chemical synthesis instrument that optimizes the reaction conditions in real-time (e.g., the application of microwave energy) based on the received and analyzed data.

It is a further object of the present invention to provide a microwave-assisted chemical synthesis method that automatically optimizes the reaction conditions in real-time by non-invasively measuring the scattered photons with a radiation detector and controlling the input of microwave energy based on the measurements.

The foregoing and other objects and advantages of the invention and the manner in which the same are accomplished will become clearer based on the following detailed description taken in conjunction with the accompanying drawings in which:

DETAILED DESCRIPTION

Figure 1:
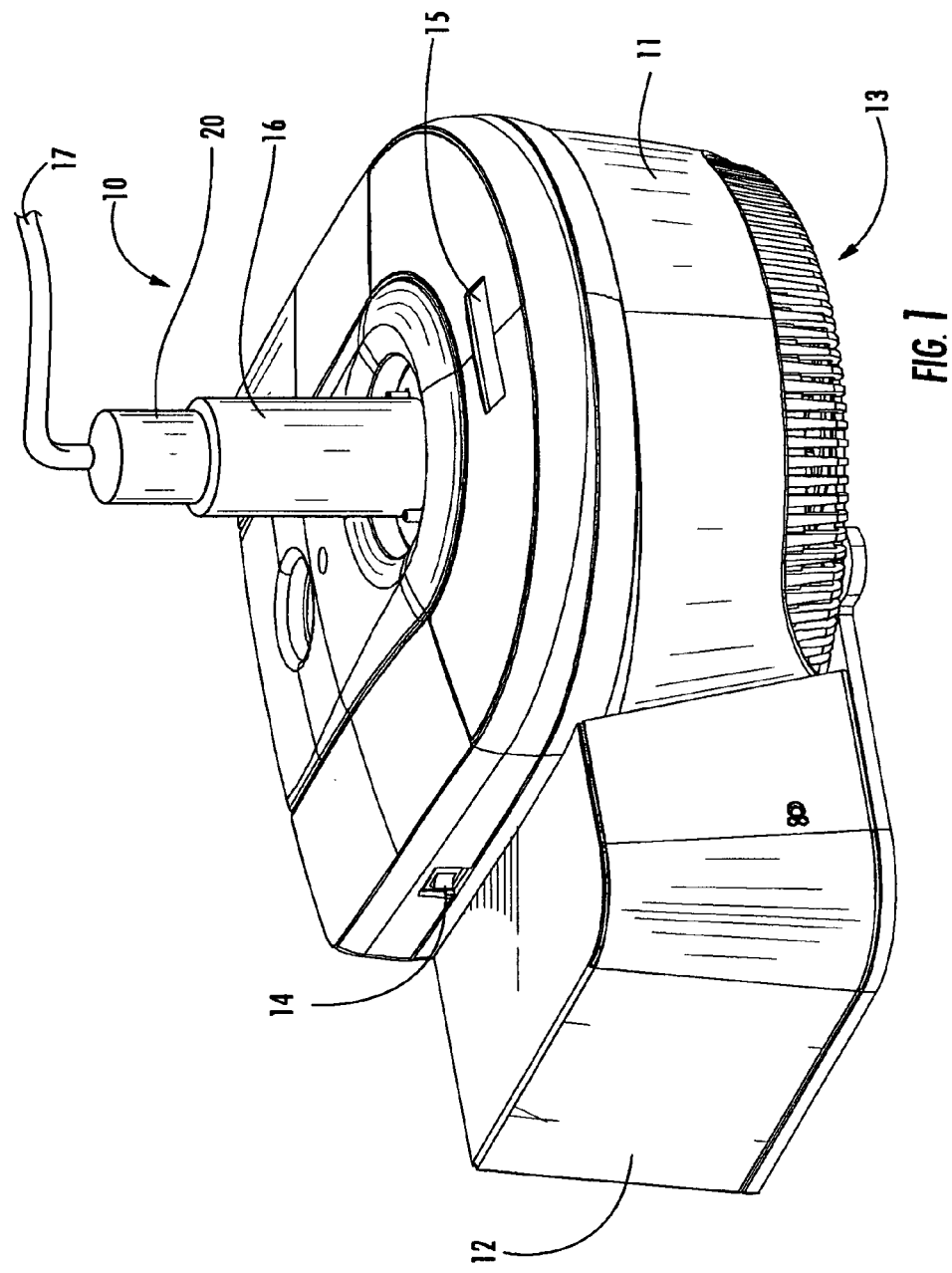
FIG. 1 is a perspective view of an instrument and vessel assembly according to the present invention.

In a first embodiment, the invention is an instrument 10 (FIG. 1) for performing microwave-assisted chemical synthesis. The instrument 10 includes a microwave apparatus housing 11 and a Raman detector housing 12, typically made of rugged plastic or metal. The housings 11,12 protect internal components described herein. At least one of the housings 11,12 is vented with slotted apertures 13 to facilitate cooling of internal components. FIG. 1 further illustrates other general features of the instrument 10, such as a power switch 14, a status display 15, and a microwave-transparent reaction vessel 20. The reaction vessel 20 is surrounded by an attenuator 16 and may be fed using a feed tube 17. The attenuator 16 prevents microwave energy from escaping the vessel 20.

Figure 2:
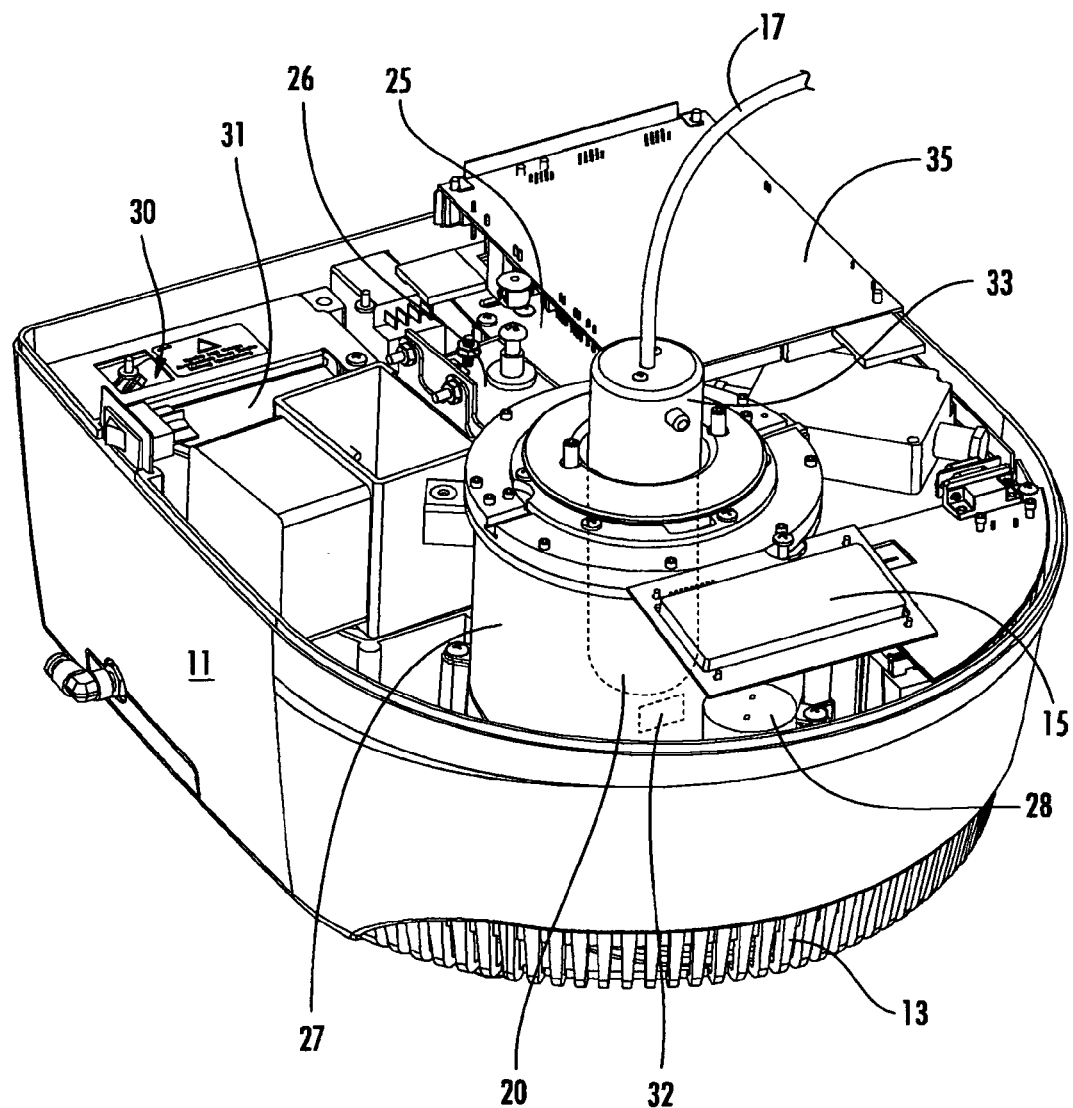
FIG. 2 is a partial perspective view of the microwave reaction vessel and microwave cavity of the present invention.

FIG. 2 is a partial perspective view of the microwave apparatus housing 11 and various internal components therein. Briefly, FIG. 2 illustrates a microwave source 25, a waveguide 26, a microwave cavity 27, a stir motor 28, a fan 30, its accompanying housing 31, and a pressure transducer 33. Also shown are the reaction vessel 20, the feed tube 17, and various electronics 35 to control, for example, the status display 15.

Useful microwave sources are well known to those of ordinary skill in the art and can include magnetrons, klystrons, and solid state devices. In the instrument 10, microwaves travel from the source 25 through the waveguide 26 to the microwave cavity 27. The sample in the reaction vessel 20 absorbs the microwave energy as the energy enters the microwave cavity 27. In this manner, the microwave cavity 27 is in microwave communication with the microwave source 25.

The waveguide 26 is constructed of a material that reflects microwaves inwardly and prevents them from escaping in any undesired manner. Typically, such material is an appropriate metal which, other than its function for confining microwaves, can be selected on the basis of its cost, strength, formability, corrosion resistance, or any other desired or appropriate criteria. In preferred embodiments of the invention, the metal portions of the waveguide 26 and cavity are formed of stainless steel.

As is the case with other kinds of chemistry, it can be advantageous in microwave-assisted organic chemistry to stir and mix the sample in the reaction vessel 20. This is accomplished, for example, using a motor 28 to drive a magnetic stirrer, such as that described in U.S. Patent Publication No. 2003/0170149 to Jennings, incorporated entirely herein by reference.

The fan 30 serves to cool the electronics and the microwave source 25 portions of the instrument 10, as well as helping to keep the microwave cavity 27 from becoming overheated in the presence of ongoing chemical reactions. Other than having the capacity to appropriately cool the instrument and the cavity, the nature or selection of the fan 30 can be left to the individual discretion of those with skill in this art. In a typical embodiment, the fan 30 is mounted in a housing 31 to direct the flow of air across the electronics and the microwave source 25 to cool them more efficiently.

Figure 3:
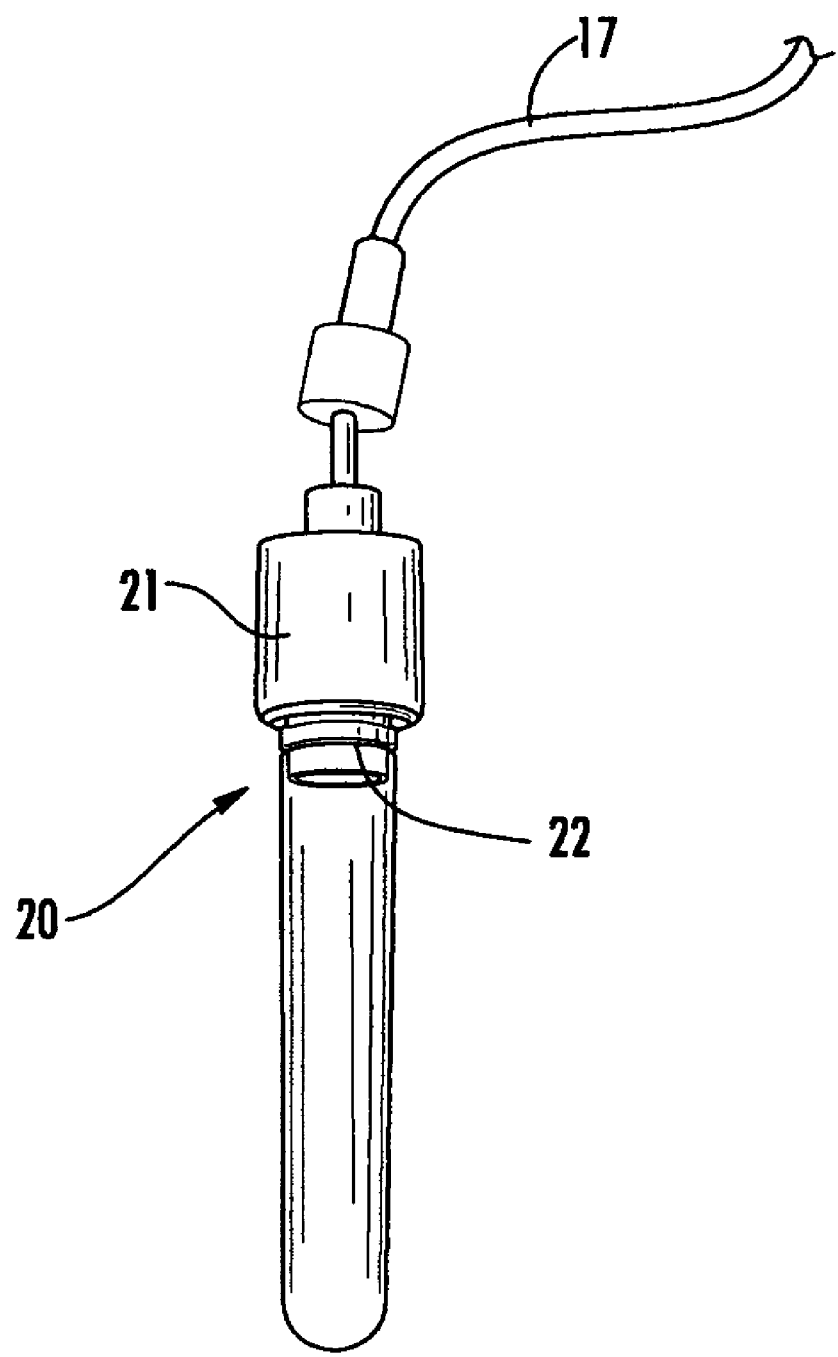
FIG. 3 is a perspective view illustrating a representative reaction vessel.

FIG. 3 illustrates an example reaction vessel 20 for holding the sample in the microwave cavity 27. The reaction vessel 20 may be a test tube shaped device, however, it may also be a round-bottom flask or other appropriate container. It should be noted that the vessel 20 shown in FIG. 3 is illustrative, and in no way limits the invention to any specific shape or volume with respect to the vessel 20. The reaction vessel 20 is further formed of a microwave-transparent material. Suitable microwave-transparent materials are well known to those of ordinary skill in the art, and include, for example, quartz, glass, and PYREX®. In preferred embodiments the reaction vessel 20 has a volume (sometimes referred to as the "working volume") of at least about 0.25 milliliters, which is a convenient size for bench-top experiments.

As also shown in FIG. 3, the reaction vessel 20 may include a fitting 21 for the feed tube 17. The fitting 21 further includes suitable sealing means 22 (e.g., o-ring seals made from a chemically inert material) to prevent the sample from leaking. Appropriate fittings are known to those of ordinary skill in the art and include, for example, threaded fittings, valves, quick-connect fittings, and hose clamps.

Figure 4:
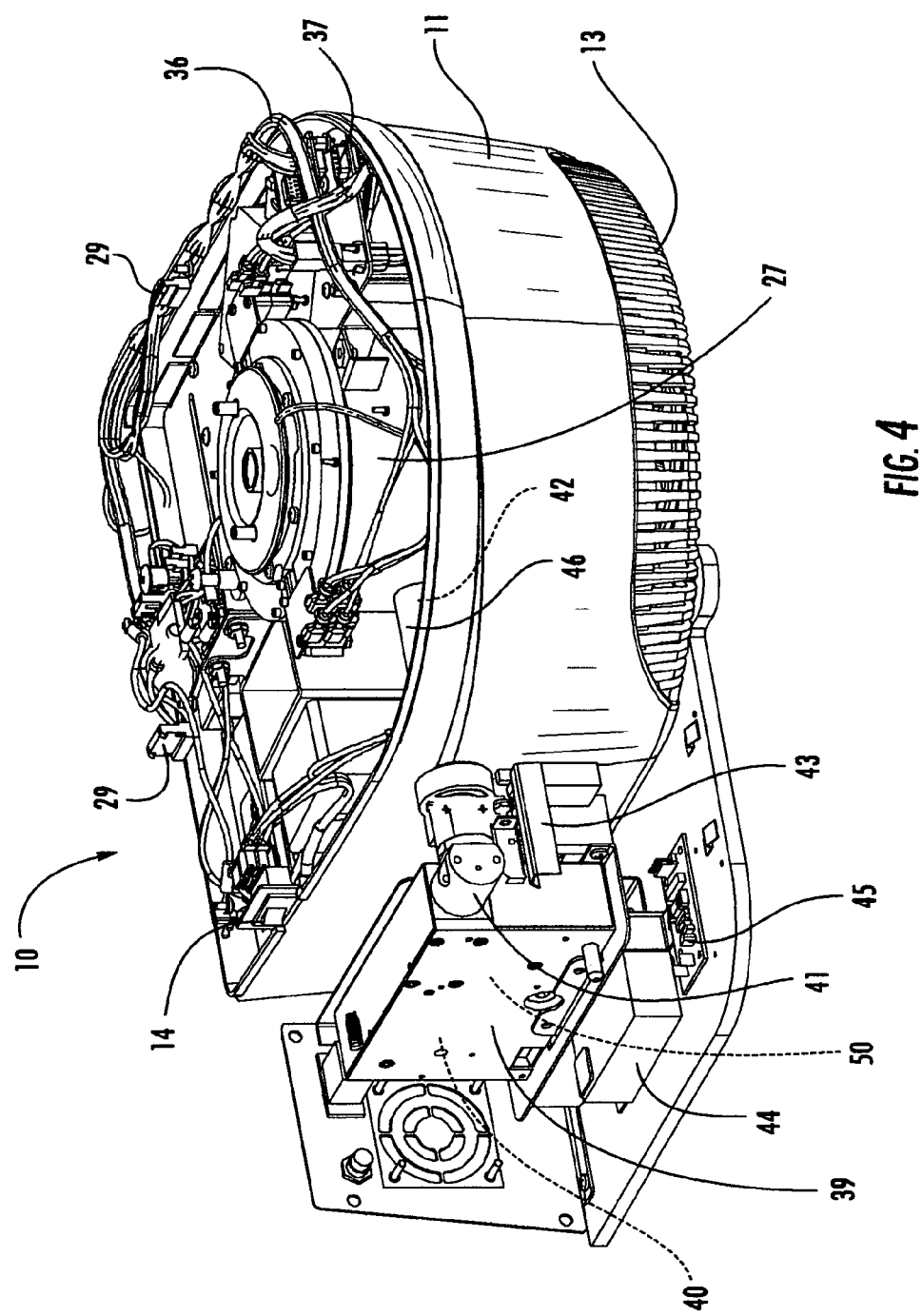
FIG. 4 is a perspective view of the instrument illustrating internal components.

FIG. 4 illustrates parts in common with FIG. 2 as well as other internal parts of the instrument 10. Retaining clips 29 hold the top portion of the instrument housing 11 in place. Also illustrated are the microwave cavity 27, the slotted apertures 13, and a power switch 14. In addition, a Raman device housing 39 encloses a substantially monochromatic radiation source 40. The source 40 is in electromagnetic communication with the microwave cavity 27 for applying substantially monochromatic light to the sample. In a preferred embodiment, the monochromatic radiation source 40 is a laser. Also enclosed by the Raman device housing 39 is a Raman detector 50 positioned for detecting Raman scattering of light from the monochromatic source 40 by the sample. The Raman detector may be, by way of example, a photomultiplier tube or a charge coupled device (CCD).

FIG. 4 further illustrates various wires 36 and electrical connectors 37. With respect to the instrument and method of the invention, the wires 36 and electrical connectors 37 are known to those of ordinary skill in the art for the routine operation of the instrument 10 and will not be discussed in further detail herein.

The instrument 10 is controlled by a controller (not shown) in signal communication with the microwave energy source 25 and the Raman detector 50 for moderating the application of microwave energy to the sample based upon the detected Raman scattering. For example, the controller is a microprocessor in electronic communication with the microwave energy source 25 and the Raman detector 50. Preferably, the microprocessor controls the microwave radiation source 25 to apply pulsed microwave energy. In this manner, the pulsed application of microwave energy avoids overheating the sample.

Microprocessors are well known in this and other arts to control many types of electronic and mechanical devices. The recent advancement in the application of semiconductor physics and silicon processing to these devices allows for smaller, more powerful microprocessors to control complex machines and processes. Discussions include, but are not limited to Dorf, *The Electrical Engineering Handbook, Second Ed.*, (1997) CRC Press LLC; and Wolf, S., *Silicon Processing for the VLSI Era*, (1990) Lattice Press.

With respect to the instrument and method of the present invention, the microprocessor may run a program defining preset parameters or respond to real-time operator input. For example, the instrument and method of the present invention can be useful as a quality control device to measure the characteristics of a sample based upon parameters defined by a computer program. Deviations from the preset parameters will prompt the microprocessor to moderate the input of microwave energy to bring the sample within specifications. Alternatively, an operator may make real-time "on-the-fly" modifications to the application of microwave energy based on the detected Raman scattering.

The microprocessor may further moderate the application of microwave energy with respect to the pressure transducer 33 (See FIG. 2). Referring to FIGS. 2 and 4, the pressure transducer 33 is in pressure communication with the sample in the reaction vessel 20 and in electronic communication with the controller for moderating the application of microwaves based upon the pressure in the reaction vessel 20 exerted by the sample.

In another embodiment, the instrument 10 is a microwave-assisted chemical synthesis instrument including a microwave source 25, a means for controlling the application of microwave energy from the microwave source 25, a microwave-transparent vessel 20 for holding a sample in wave communication with the microwave source 25, a laser energy source 40 about the vessel 20 for applying light amplified radiation into the sample, and a detector 50 positioned about the vessel 20 for detecting Raman scattering of light from the laser energy source 40 by the sample.

The means for controlling the application of microwave energy includes a microprocessor (not shown) in electronic communication with the microwave source 25 and the Raman detector 50 for receiving and analyzing data from the Raman detector 50 and simultaneously controlling the microwave source 25. Thus, the input of microwave energy to the sample is controlled and optimized in a feedback-controlled manner.

The laser energy source 40 may generate ultraviolet light (UV), visible light (VIS), infrared light (IR), or near-infrared light (NIR). Those having ordinary skill in the art will appreciate that UV light refers to the wavelength range of light from about 200 nanometers (nm) to 400 nm, VIS light refers to the wavelength range of about 380 nm to 780 nm, and IR light refers to the wavelength range of about 0.75 micrometers (μm) to 1000 μm. NIR refers to the IR spectrum that is closest to VIS light (e.g., about 785 nm). In a preferred embodiment, the laser energy source 40 is a laser diode that generates NIR light at a wavelength of about 785 nanometers. The laser energy source 40 may also be in electronic communication with the microprocessor.

The instrument 10 may further include a temperature sensor (schematically illustrated at 32 in FIG. 2) about the reaction vessel 20 for measuring the temperature of the sample. In a typical embodiment, the temperature sensor 32 is selected from the group consisting of infrared detectors, ultraviolet detectors, and fiber optic sensors. Preferably, the temperature sensor 32 is in electronic communication with the microprocessor. Accordingly, the microprocessor controls the application of microwaves from the microwave source 25 based on the measured temperature.

Figure 5:
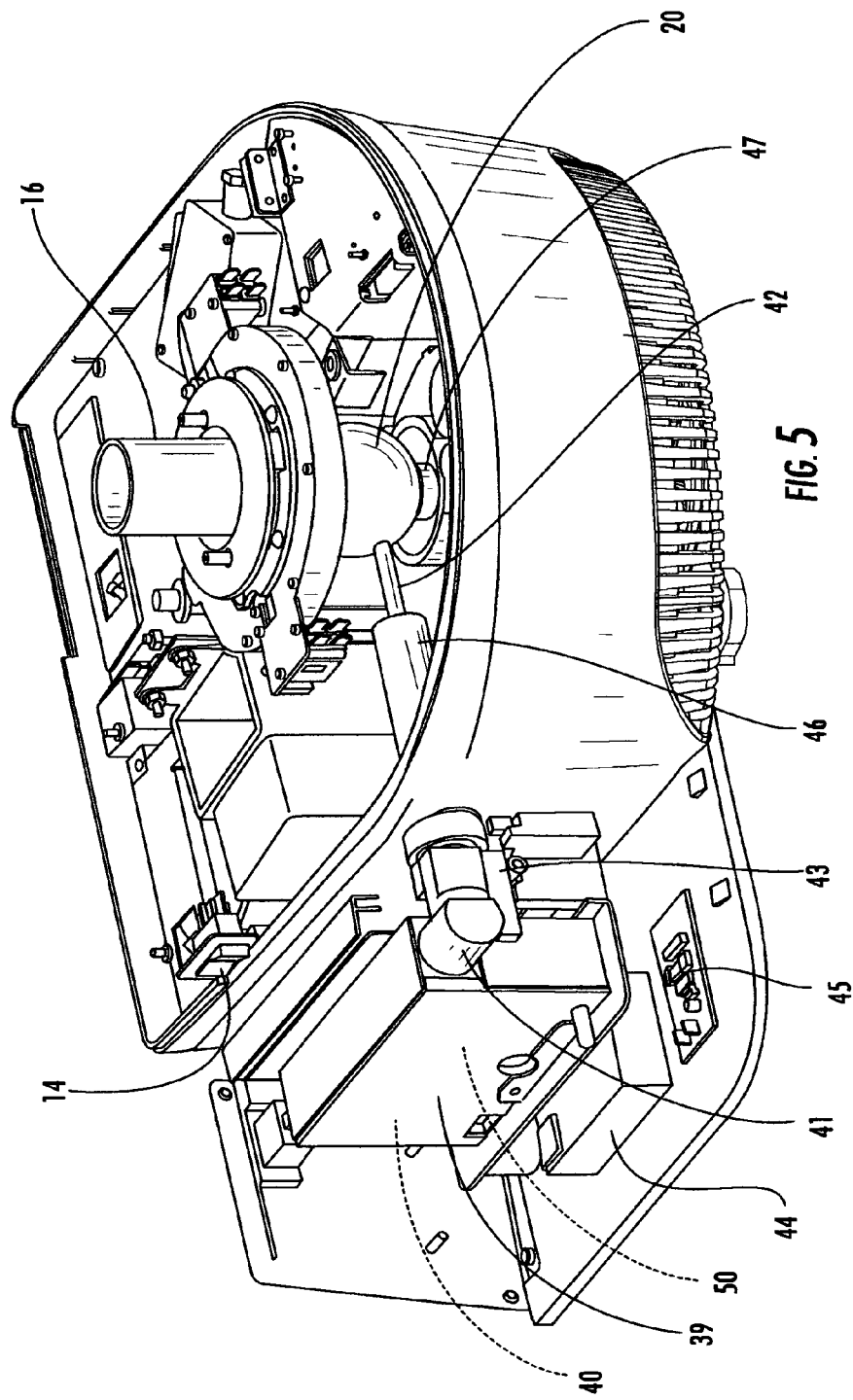
FIG. 5 is a perspective view of the instrument further illustrating internal components.

FIG. 5 illustrates the instrument in a similar manner as FIG. 4, but with the microwave cavity removed to show the reaction vessel 20, an optic tube 42, and a radio frequency stub 46. The radio frequency stub 46 prevents microwave energy from leaving the microwave cavity 27 (See FIG. 4), similar to the aforementioned attenuator 16. FIG. 5 further illustrates a mirror holder 41 for holding a mirror (not shown), an adjustment means 43 for focusing the laser onto the sample through the optic tube 42, a drive motor 44 for adjusting a reaction vessel holder 47 to accommodate various sized vessels in the microwave cavity 27, and a circuit board 45 for electronically controlling the drive motor 44.

Typically, the laser source 40, mirror (not shown), mirror holder 41, optic tube 42, grating (not shown), and Raman detector 50 are obtained as a package unit, such as the Advantage NIR Raman spectrometer supplied by DeltaNu® of Laramie, Wyoming, USA. In general terms, the grating is understood by those of ordinary skill in the art to be a spectroscope which employs a transmission or reflection grating to disperse light. Furthermore, the grating usually has a slit and a focusing means (such as a grating mirror) to focus the light dispersed by the grating into spectrum lines. In a preferred embodiment, the light is focused onto a CCD detector.

Figure 6:
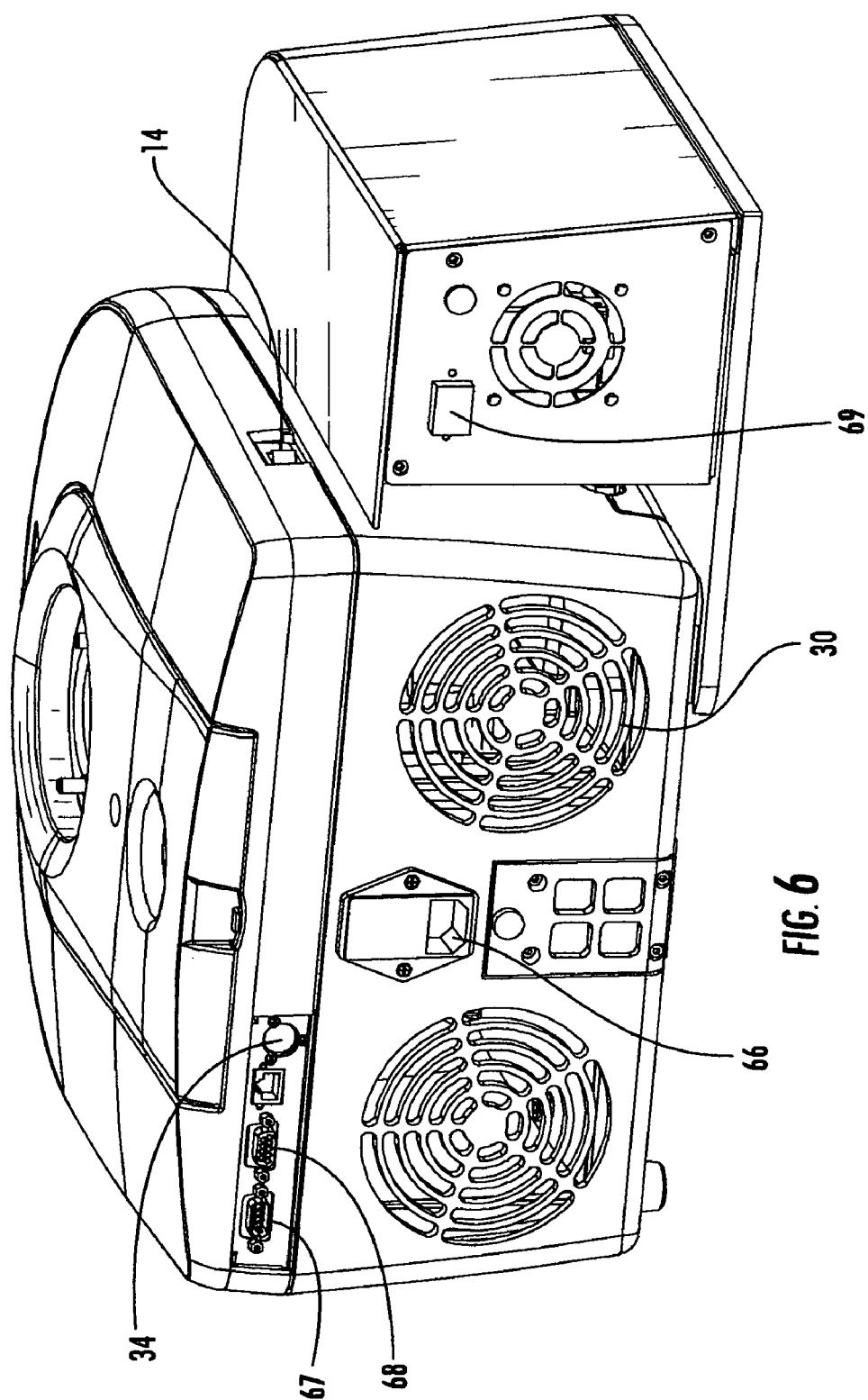
FIG. 6 is a rear perspective view of the instrument and vessel assembly according to the present invention.

FIG. 6 is a rear perspective view of the instrument housings 11,12 that illustrates some additional items. FIG. 6 illustrates the cooling fan 30, the power switch 14, and a connector 34 for the pressure transducer 33 previously described. FIG. 6 further illustrates a power cord inlet 66 and connections for peripheral devices in order to take advantage of the full capacity of the instrument. In preferred embodiments, for example, the instrument includes a parallel port 67, a serial port 68, and a universal serial bus (USB) port 69 for receiving input from or providing output to other electronic devices, particularly microprocessor based devices, such as personal computers, personal digital assistants or other appropriate devices.

In another aspect, the invention is a method for microwave-assisted chemical synthesis that includes applying microwave energy to sample reactants, propagating substantially monochromatic radiation to the sample reactants, measuring the Raman scattering of the monochromatic light from the sample, and moderating the application of microwave energy to the sample based upon the measured Raman scattering. In a preferred embodiment, the steps of applying, propagating, measuring, and moderating are simultaneously controlled by a microprocessor.

By way of example and with respect to the instrument of the invention, the method includes measuring and analyzing the Raman scattering of light from the sample before, during, and after the application of microwave energy to the sample. A laser energy pulse from the laser source projects to the mirror, through the optic tube, and into the sample. The subsequent Raman scattering of light is collected through the optic tube, onto the grating, and into a CCD detector. The raw data from the detector is read by the microprocessor. Microwave energy input is modified based on real-time feedback from the sample and with respect to the microprocessor program parameters. The microprocessor further stores the measured information (i.e., data) in electronic format. In this manner, the reaction conditions are optimized based on real-time data from the Raman detector.

The microprocessor program parameters include, but are not limited to, monitoring and moderating the temperature, reaction time, pressure, depletion of sample reactants, percentage of sample reactants converted to products, and the formation of unwanted byproducts. Thus, the step of moderating the application of microwave energy to the sample also takes into consideration the real-time measurements of the indicated parameters to automatically optimize the reaction conditions with respect to the above parameters to achieve a desired result.

Monitoring the temperature of the sample reactants may be accomplished using a temperature sensor selected from the group consisting of infrared detectors, ultraviolet detectors, and fiber optic sensors. Accordingly, the moderation of microwave energy input may be based upon the monitored temperature.

With respect to the instrument of the invention, the step of applying microwave energy to the sample reactants includes applying microwave energy to the sample reactants in a microwave-transparent reaction vessel. Furthermore, the application of microwave energy may be pulsed for variable lengths of time depending on the sample volume. Thus, overheating the sample is avoided. Sample overheating may be further avoided by actively cooling the sample (i.e., cooling the sample using the aforementioned fan).

The step of propagating substantially monochromatic radiation to the sample reactants includes propagating laser light to the sample. In a preferred embodiment, the wavelength of the laser light is about 785 nanometers.

In order to achieve the best possible data from the sample, the method of the invention further includes focusing the laser onto the sample. The step of focusing may be accomplished manually or automatically. The focus distance is calibrated with a standard reference, typically cyclohexane. Other standard references are known to those having ordinary skill in the art. The best results are achieved when the focal point is slightly inside the reaction vessel wall.

Measuring the Raman scattering of monochromatic light from the sample is achieved by collecting and analyzing the light scattered from the sample with the aid of the detector and the microprocessor. As previously mentioned, the detector may be a photomultiplier tube or a CCD.

Intense irradiation with light can cause fluorescence that is stronger than the Raman signal. Thus, analyzing the light scattered from the sample may include subtracting fluorescence information. In some instances, the fluorescence data contains useful chemical information (e.g., minerals). In other instances where the fluorescence information is unnecessary or interferes with the Raman data, the microprocessor may be programmed to subtract the fluorescence information.

The microprocessor revises the Raman scattering measurements at least about once per second to generate a spectrogram. Typically, the spectrogram is stored in electronic format in memory associated with the microprocessor and displayed on a peripheral device, such as a computer monitor. The spectrograms are calculated and generated by the microprocessor using Euclidian geometry, specifically a non-linear curve fit formula. Briefly, the non-linear curve fit formula measures the change at each point on the X and Y axes. For an in-depth discussion of Euclidian principles, the reader is directed to an appropriate text on the subject by Posamentier (Alfred S. Posamentier, *Advanced Euclidean Geometry: Excursions for Secondary Teachers and Students,* 2005, Key Curriculum Press). The technique is, however, well understood by those of ordinary skill in this art.

As previously mentioned, the method of the invention provides for real-time modifications regarding microwave energy input with respect to the microprocessor program parameters. This includes the addition of liquids or solids as required before, during, and after the method. By way of non-limiting example, the method may further include adding a coupling reagent to the sample to facilitate the conversion of sample reactants to products. Another example includes adding a catalyst reagent to the sample to accelerate the rate of the reaction. With respect to the instrument of the invention, the addition of liquids or solids is accomplished using the aforementioned feed tube.

Those having ordinary skill in the art will appreciate that with respect to the instrument of the invention, the method allows for the subtraction of baseline spectra immediately before or after the addition of liquids or solids. In this manner, any effect caused by the addition of liquids or solids can be measured from a "reset" baseline.

Additionally, the instrument and method of the present invention may be usefully and successfully combined with other advantageous systems and techniques in microwave-assisted chemistry. These can include, but are not limited to continuous flow systems and techniques such as those set forth in commonly assigned U.S. Pat. No. 6,867,400; and systems and techniques for synthesis (or other reactions) using heterogeneous or highly viscous starting materials such as the instrument and method set forth in commonly assigned U.S. Patent Publication No. 2005/0045625A1. Both references are incorporated entirely herein by reference.

In the specification and the drawings, typical and preferred embodiments of the invention have been disclosed. Specific terms have been used only in a generic and descriptive sense, and not for purposes of limitation. The scope of the invention is set forth in the following claims.

What is claimed is:

1. An apparatus for microwave-assisted chemical synthesis, comprising:
    a source of microwave radiation;
    a microwave cavity in wave communication with said source for holding a sample in said cavity during the application of microwave energy to said cavity from said source;
    a substantially monochromatic radiation source in optical communication with said cavity for applying substantially monochromatic light to the sample in said cavity;
    a detector positioned for detecting Raman scattering of light from said monochromatic source by the sample; and
    a controller in signal communication with said microwave energy source and said Raman scattering detector for moderating the application of microwave energy to the sample based upon the detected Raman scattering from the sample in said cavity.

2. The apparatus according to claim 1 wherein said microwave source is selected from the group consisting of magnetrons, klystrons, and solid state devices.

3. The apparatus according to claim 1 wherein said controller further comprises a microprocessor in electronic communication with said microwave energy source and said detector.

4. The apparatus according to claim 3 wherein said microprocessor controls said source of microwave radiation to apply pulsed microwave energy.

5. A microwave-assisted chemical synthesis instrument according to claim 3 further comprising:
    a microwave-transparent vessel for holding a sample in wave communication with said microwave source;
    and wherein said radiation source comprises a laser.

6. The instrument according to claim 5 wherein said laser energy source generates visible light.

7. The instrument according to claim 5 wherein said laser energy source generates infrared light.

8. The instrument according to claim 5 wherein said laser energy source generates near-infrared light.

9. The instrument according to claim 8 wherein the near-infrared light is a wavelength of about 785 nanometers.

10. The instrument according to claim 5 wherein said laser energy source is in electronic communication with said microprocessor.

11. The instrument according to claim 5 further comprising a temperature sensor about said microwave-transparent vessel for measuring the temperature of the sample.

12. The instrument according to claim 11 wherein said temperature sensor is selected from the group consisting of infrared detectors, ultraviolet detectors, and fiber optic sensors.

13. The instrument according to claim 11 wherein said temperature sensor is in electronic communication with said microprocessor.

14. The instrument according to claim 13 wherein said microprocessor controls the application of microwaves from said microwave source based upon the measured temperature.

15. The instrument according to claim 5 wherein said microprocessor stores said data from said detector in electronic format.

16. The apparatus according to claim 1 further comprising a waveguide between said source and said cavity.

17. The apparatus according to claim 1 further comprising a microwave-transparent reaction vessel for holding the sample in said cavity.

18. The apparatus according to claim 17 wherein said microwave-transparent vessel further comprises a fitting to fit enclosably over an opening in said vessel, said fitting having at least one feed tube attached thereon for adding liquids or solids to said sample.

19. The apparatus according to claim 18 wherein said microwave-transparent vessel comprises glass.

20. The apparatus according to claim 18 wherein said microwave-transparent vessel comprises quartz.

21. The apparatus according to claim 18 wherein said microwave-transparent vessel comprises PYREX.

22. The apparatus according to claim 17 further comprising a pressure transducer in pressure communication with said sample in said vessel and in electronic communication with said controller for moderating the application of microwaves based upon the pressure in the vessel exerted by the sample.

23. The apparatus according to claim 1 wherein said monochromatic radiation source comprises a laser.

24. The apparatus according to claim 1 wherein said detector is a photomultiplier tube.

25. The apparatus according to claim 1 wherein said detector is a charge coupled device.

26. A method for microwave-assisted chemical synthesis, comprising:
applying microwave energy to sample reactants in a microwave cavity;
propagating substantially monochromatic radiation to the sample reactants in the cavity;
measuring the Raman scattering of the monochromatic light from the sample in the cavity; and
moderating the application of microwave energy to the sample in the cavity based upon the measured Raman scattering.

27. The method of claim 26 wherein the steps of applying, propagating, measuring, and moderating are simultaneously controlled by a microprocessor.

28. The method of claim 27 wherein the step of applying microwave energy to the sample reactants comprises applying microwave energy to the sample reactants in a microwave-transparent reaction vessel.

29. The method of claim 28 wherein the step of moderating the application of microwave energy comprises moderating the application of microwaves based upon the monitored temperature.

30. The method of claim 28 wherein the step of applying microwave energy to the sample further comprises the step of monitoring the pressure within the reaction vessel with a pressure transducer.

31. The method of claim 27 further comprising the step of monitoring the temperature of the sample reactants with a temperature sensor selected from the group consisting of infrared detectors, ultraviolet detectors, and fiber optic sensors.

32. The method of claim 31 comprising actively cooling the sample.

33. The method of claim 27 wherein the step of applying microwave energy further comprises applying pulsed microwave energy for variable lengths of time depending on the sample volume.

34. The method of claim 27 wherein the step of propagating substantially monochromatic light comprises propagating laser light to the sample.

35. The method of claim 34 comprising propagating the laser light at a wavelength of about 785 nanometers.

36. The method of claim 27 wherein the step of measuring the Raman scattering further comprises storing the measured information in electronic format.

37. The method of claim 27 wherein the step of measuring the Raman scattering further comprises correcting the scattering measurements by subtracting fluorescence information.

38. The method of claim 27 wherein the step of measuring the Raman scattering further comprises revising the measurements at least about once per second.

39. The method of claim 27 wherein the step of measuring the Raman scattering further comprises performing Euclidian calculations to generate a spectrogram.

40. The method of claim 39 wherein the step of generating a spectrogram further comprises storing the spectrogram in electronic format.

41. The method of claim 27 wherein the step of propagating substantially monochromatic radiation comprises focusing laser energy onto the sample.

42. The method of claim 41 wherein the step of focusing is performed automatically.

43. The method of claim 41 wherein the step of focusing is performed manually.

44. The method of claim 41 wherein the step of focusing is calibrated using a standard reference.

45. The method of claim 44 wherein the standard reference comprises cyclohexane.

46. The method of claim 27 wherein the step of moderating the application of microwave energy further comprises moderating the input of microwave energy upon measured Raman scattering that indicates the depletion of sample reactants.

47. The method of claim 27 wherein the step of moderating the application of microwave energy further comprises moderating the input of microwave energy upon measured Raman scattering that indicates a desired percentage of sample reactants converted to products.

48. The method of claim 27 wherein the step of moderating the application of microwave energy further comprises moderating the input of microwave energy upon measured Raman scattering that indicates the formation of unwanted byproducts.

49. The method of claim 27 wherein the step of moderating the application of microwave energy further comprises moderating the input of microwave energy at a particular time.

50. The method of claim 27 wherein the step of moderating the application of microwave energy further comprises moderating the input of microwave energy at a particular pressure.

51. The method of claim 26 further comprising adding a coupling reagent to the sample to facilitate the conversion of sample reactants to products.

52. The method of claim 26 further comprising adding a catalyst reagent to the sample to accelerate the rate of the reaction.

* * * * *